United States Patent
McKinnon et al.

(10) Patent No.: US 8,142,509 B2
(45) Date of Patent: Mar. 27, 2012

(54) PATELLAR COMPONENTS

(75) Inventors: Brian W. McKinnon, Bartlett, TN (US); Jason K. Otto, Plantation, FL (US)

(73) Assignee: Smith & Nephew, Inc., Memphis, TN (US)

( * ) Notice: Subject to any disclaimer, the term of this patent is extended or adjusted under 35 U.S.C. 154(b) by 240 days.

(21) Appl. No.: 12/159,805

(22) PCT Filed: Jan. 23, 2007

(86) PCT No.: PCT/US2007/002041
§ 371 (c)(1),
(2), (4) Date: Aug. 14, 2008

(87) PCT Pub. No.: WO2007/102951
PCT Pub. Date: Sep. 13, 2007

(65) Prior Publication Data
US 2008/0300689 A1    Dec. 4, 2008

Related U.S. Application Data

(60) Provisional application No. 60/761,296, filed on Jan. 23, 2006, provisional application No. 60/761,297, filed on Jan. 23, 2006, provisional application No. 60/761,298, filed on Jan. 23, 2006.

(51) Int. Cl.
*A61F 2/38* (2006.01)
(52) U.S. Cl. .................. 623/20.18; 623/20.19; 623/20.2
(58) Field of Classification Search ..... 623/20.18–20.21
See application file for complete search history.

(56) References Cited

U.S. PATENT DOCUMENTS

| | | | |
|---|---|---|---|
| 3,878,566 A | 4/1975 | Bechtol | |
| 3,927,423 A | 12/1975 | Swanson | |
| 4,007,495 A | 2/1977 | Frazier | |
| 4,094,017 A | 6/1978 | Matthews et al. | |
| 4,158,894 A | 6/1979 | Worrell | |
| 4,178,641 A | 12/1979 | Grundei et al. | |
| 4,207,627 A | 6/1980 | Cloutier | |
| 4,285,070 A | 8/1981 | Averill | |
| 4,353,135 A * | 10/1982 | Forte et al. | 623/20.2 |
| 4,470,158 A | 9/1984 | Pappas | |
| 4,633,862 A | 1/1987 | Petersen | |
| 4,888,021 A | 12/1989 | Forte et al. | |
| 4,944,756 A | 7/1990 | Kenna | |
| 4,964,867 A | 10/1990 | Boger | |
| 5,011,496 A | 4/1991 | Forte et al. | |
| 5,019,104 A | 5/1991 | Whiteside et al. | |
| 5,021,061 A | 6/1991 | Wevers et al. | |
| 5,035,700 A | 7/1991 | Kenna | |
| 5,098,436 A | 3/1992 | Ferrante et al. | |
| 5,197,986 A | 3/1993 | Mikhail | |

(Continued)

FOREIGN PATENT DOCUMENTS
DE        9116507 U1    12/1992
(Continued)

*Primary Examiner* — David H Willse
*Assistant Examiner* — Javier Blanco
(74) *Attorney, Agent, or Firm* — Kilpatrick Townsend & Stockton LLP

(57) ABSTRACT

Embodiments of the present invention provide patellar component designs that are optimally shaped to help reduce shear force and accommodate slight implantation error. Further, they help lessen anterior knee pain, particularly during deep-flexion activities and help ease the transition during the range of knee movement in a controlled way.

23 Claims, 15 Drawing Sheets

U.S. PATENT DOCUMENTS

| | | | |
|---|---|---|---|
| 5,201,773 A | 4/1993 | Carideo et al. |
| 5,222,955 A | 6/1993 | Mikhail |
| 5,236,462 A | 8/1993 | Mikhail |
| 5,246,460 A | 9/1993 | Goodfellow et al. |
| 4,221,006 A | 1/1994 | Thomas |
| 5,284,482 A | 2/1994 | Mikhail |
| 5,330,532 A | 7/1994 | Ranawat |
| 5,383,937 A | 1/1995 | Mikhail |
| 5,395,401 A | 3/1995 | Bahler |
| 5,413,604 A | 5/1995 | Hodge |
| 5,437,676 A | 8/1995 | Bouraly et al. |
| 5,480,443 A | 1/1996 | Elias |
| 5,486,177 A | 1/1996 | Mumme et al. |
| 5,520,692 A | 5/1996 | Ferrante |
| 5,522,901 A | 6/1996 | Thomas et al. |
| 5,536,271 A | 7/1996 | Daly et al. |
| 5,580,353 A | 12/1996 | Mendes et al. |
| 5,593,450 A | 1/1997 | Scott et al. |
| 5,609,640 A | 3/1997 | Johnson |
| 5,609,644 A | 3/1997 | Ashby |
| 5,702,459 A | 12/1997 | Hummer |
| 5,702,467 A | 12/1997 | Gabriel et al. |
| 5,716,360 A | 2/1998 | Baldwin et al. |
| 5,723,016 A | 3/1998 | Minns et al. |
| 5,824,105 A | 10/1998 | Ries et al. |
| 5,871,540 A | 2/1999 | Weissman et al. |
| 5,885,298 A | 3/1999 | Herrington et al. |
| 5,941,884 A | 8/1999 | Corvelli et al. |
| 6,146,423 A | 11/2000 | Cohen et al. |
| 6,159,246 A | 12/2000 | Mendes et al. |
| 6,277,121 B1 | 8/2001 | Burkinshaw et al. |
| 6,589,248 B1 | 7/2003 | Hughes |
| 6,602,258 B1 | 8/2003 | Katz |
| 6,602,292 B2 | 8/2003 | Burkinshaw |
| 6,709,460 B2 | 3/2004 | Merchant |
| 6,800,094 B2 | 10/2004 | Burkinshaw |
| 6,802,864 B2 | 10/2004 | Tornier |
| 6,866,667 B2 | 3/2005 | Wood et al. |
| 6,905,514 B2 | 6/2005 | Carignan et al. |
| 7,691,149 B2 | 4/2010 | Brown et al. |
| 7,713,305 B2 | 5/2010 | Ek |
| 7,758,651 B2 | 7/2010 | Chauhan et al. |
| 2003/0033018 A1 | 2/2003 | Merchant |
| 2003/0120346 A1 | 6/2003 | Mercinek et al. |
| 2003/0181984 A1 | 9/2003 | Abendschein |
| 2004/0167630 A1 | 8/2004 | Rolston |
| 2005/0043807 A1 | 2/2005 | Wood |
| 2005/0090396 A1 | 4/2005 | Feucht et al. |
| 2005/0143830 A1 | 6/2005 | Marcinek et al. |
| 2005/0171612 A1 | 8/2005 | Rolston |
| 2005/0251065 A1 | 11/2005 | Henning et al. |
| 2007/0118141 A1 | 5/2007 | Marchyn et al. |
| 2007/0162142 A1 | 7/2007 | Stone |
| 2007/0198022 A1 | 8/2007 | Lang et al. |
| 2008/0188942 A1 | 8/2008 | Brown et al. |
| 2008/0300689 A1 | 12/2008 | McKinnon et al. |
| 2009/0036993 A1 | 2/2009 | Metzger |
| 2009/0326661 A1 | 12/2009 | Wright et al. |
| 2009/0326662 A1 | 12/2009 | Goldstein et al. |
| 2010/0030223 A1 | 2/2010 | Keller |
| 2010/0057211 A1 | 3/2010 | Cuckler et al. |
| 2010/0131068 A1 | 5/2010 | Brown et al. |
| 2010/0160915 A1 | 6/2010 | Chauhan et al. |
| 2010/0160917 A1 | 6/2010 | Fitz et al. |
| 2010/0174379 A1 | 7/2010 | McMinn |

FOREIGN PATENT DOCUMENTS

| | | | |
|---|---|---|---|
| EP | 0327297 A2 | 8/1989 |
| EP | 0214212 B1 | 9/1989 |
| EP | 0438918 A1 | 7/1991 |
| EP | 0502737 A1 | 9/1992 |
| EP | 0556997 A1 | 8/1993 |
| EP | 575232 | 12/1993 |
| EP | 0582514 A | 2/1994 |
| EP | 0497955 B1 | 9/1994 |
| EP | 474320 | 7/1995 |
| EP | 0676182 A1 | 10/1995 |
| EP | 0691831 | 1/1996 |
| EP | 0736292 A2 | 10/1996 |
| EP | 0812581 A2 | 12/1997 |
| EP | 0983750 A1 | 3/2000 |
| EP | 1013232 A2 | 6/2000 |
| FR | 2700260 A1 * | 7/1994 |
| GB | 2247407 A | 3/1992 |
| GB | 2277034 A | 10/1994 |
| WO | WO 9115168 | 10/1991 |
| WO | WO 9203109 | 3/1992 |
| WO | WO 9213503 | 8/1992 |
| WO | WO 9218069 | 10/1992 |
| WO | WO 9314719 | 8/1993 |
| WO | WO 9413214 | 6/1994 |
| WO | WO 9422397 | 10/1994 |
| WO | WO 9725006 | 7/1997 |
| WO | WO 9743985 | 11/1997 |
| WO | WO 9806343 | 2/1998 |
| WO | WO 03013339 A2 | 2/2003 |
| WO | WO 03070127 A1 | 8/2003 |

* cited by examiner

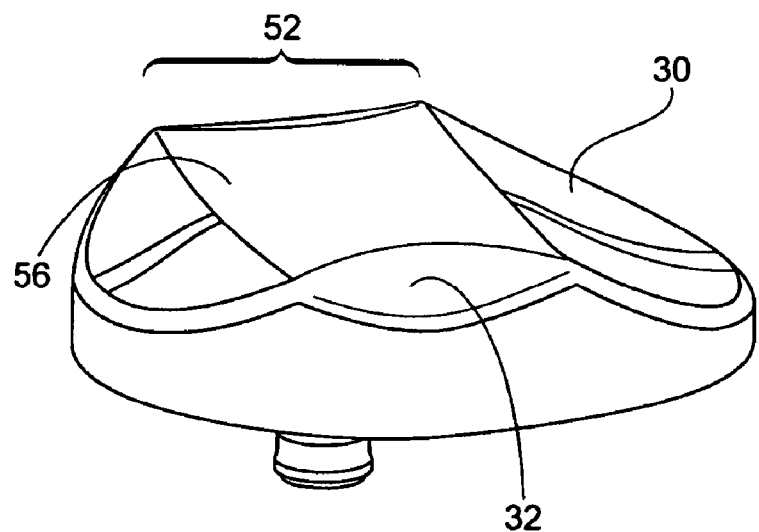
FIG. 11
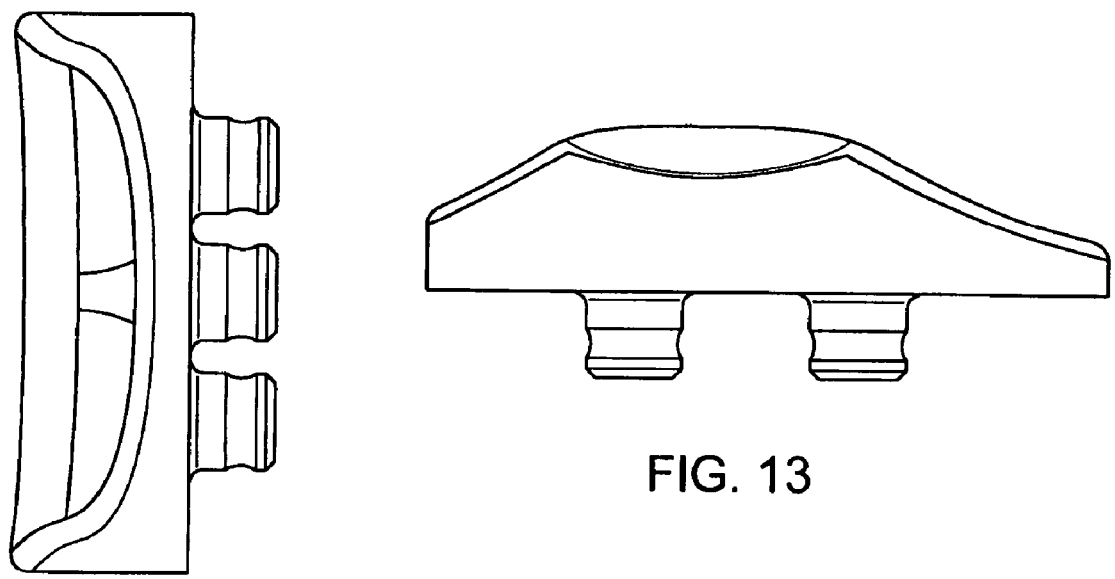
FIG. 12
FIG. 13

PATELLAR COMPONENTS

CROSS REFERENCE TO RELATED APPLICATIONS

This application is the United States national phase of International Application No. PCT/US2007/002041 filed on Jan. 23, 2007 and published in English on Sep. 13, 2007 as International Publication No. WO 2007/102951 A2, which application claims the benefit of U.S. Provisional Application Ser. No. 60/761,296 filed on Jan. 23, 2006 entitled "Low Shear Force Patella;" U.S. Provisional Application Ser. No. 60/761,297 filed on Jan. 23, 2006 entitled "Controlled Constraint Anatomic Patella;" and U.S. Provisional Application Ser. No. 60/761,298 filed on Jan. 23, 2006 entitled "Convex Oval Patella," the entire contents of each of which are hereby incorporated by reference.

BACKGROUND OF THE INVENTION

The present invention relates generally to patellar components that are designed to form a patella portion (or knee cap) that replaces a part of a natural patella or knee cap, and particularly to patellar components that are designed to cooperate and articulate against a femoral component of a total knee prosthesis. Also provided are methods for implanting the described patellar components.

Joint replacement, and particularly knee replacement, has become increasingly widespread. Various knee prostheses and procedures have been developed to treat the debilitating effects of knee joint deterioration (e.g., such as that caused by arthritis, injury, or disease). A fairly common procedure used to repair a patient's knee is total knee replacement, in which the tibia is resected and replaced with a tibial component, and the femur is resected and replaced with a femoral component. In some instances, the surgeon will also replace the articulating surface on the posterior aspect of the patella where it interfaces with the femoral component, which can help improve the results of total or partial knee replacements.

The primary function of the patella is to increase the efficiency of the quadriceps muscles and to serve as a connection between the quadriceps tendon and the patellar tendon. The patella has a ridge on its posterior side which slides in a groove between the femoral condyles, referred to as the patellar track. The patella, patellar track, and condyles act together as a low friction pulley and lever for the quadriceps tendon.

As shown in FIG. 1, during knee replacement surgery, a prosthetic patellar component 2 can be affixed to the natural patella 4 so that its posterior side 6 contacts the femoral component 8 during flexion and extension of the knee. The patellar component 2 then tracks the trochlear groove 9 of the femoral component (the line that separates the femoral condyles) during flexion and extension of the knee.

In order to implant the patellar component 2, a part of the natural patella bone is removed, and an implant is secured thereto. Some implants are "inset," meaning that a shallow hole is drilled into the bone using a counterbore so that the implant lies about flush with the bone. Other types are "onset," which means that the back of the patella is planed off and the implant is placed on top of the flat bone. The invention described in this application transcends these types of implants and can be used for both.

The maximum range of motion for a natural knee is about 150-160 degrees. By contrast, most knee replacements achieve only about 110-120 degrees of flexion. Some of this gap can be attributed to scarring within the knee joint and other physical conditions, but the remainder can be attributed primarily to failure of current implants to provide the proper prosthetic component geometries that take into consideration the natural kinematics of the knee.

Thus, despite the relative success of some products on the market, many patellar components tend to fail after about five to fifteen years. Part of the reason they fail is due to excessive wear at certain regions of the component or loosening at the bone/component interface. For example, with a dome patellar component, one reason for failure is the downward forces of the femoral component acting on the patellar component during flexion can cause the pegs that extend from the patellar component and attach the component to the natural patella to weaken and break. Shear forces that are applied directly to the implant change during knee motion, and they increase as the knee is moved deeper into flexion. For example, at different angles of flexion, the contact stresses across the patello-femoral interface move outward towards the periphery of the interface and increase as knee flexion increases. During knee flexion, the patella itself flexes and the contact point moves superiorly on the component articular surface. At this location, the contact force (normal to the articular surface of the component) creates backside compressive forces and backside shear forces.

For example, when a person is standing upright, the normal line of pressure that the femoral component 8 exerts on a button or dome patellar component 2 points at or near the center of the component dome. An example of the line of pressure is shown in FIG. 2, by arrow A. During flexion (e.g., as a person squats), the flexion of the knee increases and causes the contact point between the femoral component and the patellar component to roll deeper in the trochlear groove and into the condyles. The line of pressure also swings up from the center of the dome toward the upper part of the component. In full flexion, the line of pressure is no longer normal to the natural patella, but is directed downward, pointing down toward an upper portion of the patellar component, as shown by arrow B in FIG. 3. In full flexion, the force vector applies pressure at an upper portion of the patella. It essentially tries to "push" the button patella component off of the patellar bone surface. This force will be referred to as shear force. Part of the reason this occurs is because of the button patella's axis-symmetric dome-like shape.

A useful analogy for illustrating shear force is to consider a dome-shaped paperweight on a desk top. If someone applies pressure at the center of the dome, the paperweight stays in place. This is analogous to a person standing upright, with the force (i.e., compressive force) of the femoral component being directed at the center of the patellar dome. Referring back to the paperweight example, if a person swings the pressure point normal to the surface and toward an upper part of the paperweight (e.g., toward one of the edges), the paperweight will slide along the surface of the desk. This is analogous to the knee in flexion, where the force of the femoral component is directed toward an upper part of the patellar component. In this position, the pegs that attach the patellar component to the patella are particularly stressed. In fact, a number of artificial patella failures are due to peg failures, and these types of forces can be painful for the patient. This force is referred to as shear force, and embodiments of this invention seek to avoid or decrease shear force.

Part of the reason that shear force causes a problem with artificial patellar components and not with a natural patella is because artificial patellar components tend to be shaped like an arc or a dome, whereas the natural patella is more linear shaped. Because a natural patella is flatter, as the patella rotates during flexion and the contact vector(s) travel up the patella (note that when contact is with the condyles, there are two contact vectors, one from each condyle, and when contact is with the trochlear groove, there is a single contact vector), the force vector(s) from the femoral component still remain somewhat normal (or perpendicular) to the patella, as opposed to pointing down at an angle at the dome of a patellar component.

Under ideal conditions, anatomically-shaped patella components exhibit lower interface shear forces due to their contact condition and shape. However, they can be particularly sensitive to high contact stress edge loading due to malrotation or positioning during surgical implantation. For example, many of the highly-conforming "anatomic" patella designs offered have different levels of constraint between the trochlear groove articulation area and the intracondylar articulation area. The constraint difference is magnified in the anatomic design compared to a button (or dome) design because the anatomic design interfaces with more of the femoral surface. This magnified constraint difference causes the anatomic patellar components to shift their alignment (equilibrium) with respect to the femoral component (particularly in rotational degrees of freedom) when moving from one area to the other, which can be perceived as an instability, pain, or a clunk to the patient. The shift seems to be more aggressive during ascent, when the patella is moving from the intracondylar area into the trochlear groove. The design challenge faced is to design surfaces of patellar components that minimize the shift in constraint, while still reducing the component/bone shear forces. Such designs will hopefully reduce patient pain and prolong the life of components.

Accordingly, embodiments of the invention minimize shear force load between a patella component and the patella bone, but still provide a component that is not as sensitive to surgical mal-implantation or functional kinematics as highly-conforming "anatomically-shaped" patellas are.

Another challenge experienced by patellar component manufacturers is to design a component that lessens the shear force issues described, but that also accommodates variations introduced by surgical inaccuracy and patient anatomical variation. For example, it is difficult to position a patellar component so that it precisely matches the orientation of the patello-femoral groove geometry on the femoral component. Accordingly, most designs on the market use an axis-symmetric configuration for the bearing surface of the patellar component (as shown in FIGS. 1-3), which results in a low conformity between the patellar component part and the femoral component. With such a design, the surgeon does not need to exactly and precisely position the component in order for it to function. However, such components cause the above-described shear force problems due to their shape. Other designs have attempted to make patellar components flatter or more concave, so that they more closely approximate a natural patella, but as the components are made flatter, they are more to sensitive positioning error. Due to a lack of precise instruments, data, and information, it can be difficult to surgically arrange for the rotational positioning of an anatomic patellar component so that it precisely matches the orientation of the patello-femoral groove geometry on the femoral component. In other words, flatter components are more sensitive to mal-rotation. When non-axis-symmetric patellar components are not implanted at the proper position, it can cause ever greater wear concerns than the axis-symmetric designs discussed above.

For example, some designs provide components having saddle shaped articulating areas separated by a flat ridge. While these components theoretically allow for a larger surface contact area between the patellar component and the femoral component, they are also extremely sensitive to alignment (particularly rotational alignment and the inclination of the patellar component to the natural patellar bone). When surgical accuracy is not absolute, the error in alignment can cause edge loading and excessive fixation loading of the patellar component.

Another problem experienced by conforming, anatomically-shaped patellas (such as saddle-shaped patellas) is that they have different constraint patterns with the femoral component throughout the range of flexion. Specifically, the constraint of the patella riding in the trochlear groove is different from the constraint of the patella riding in the intracondylar area. As a consequence, the patella seeks different equilibrium positions while articulating in each zone. During the transition of the patella from the trochlear groove to the intracondylar area, there is often a readjustment translation and/or rotation movement caused by the patella arriving at a new equilibrium condition with the different constraint pattern. This movement is referred to as clunk, and it is especially apparent during extension from deep flexion. As previously mentioned, it can cause pain and may also be perceived by the patient as instability as the transition may be non-linear and possibly inconsistent from one area to another.

Accordingly, there is a need for a patellar component design that is more optimally shaped so that it can help reduce shear force, but that is also shaped to accommodate slight implantation error. There is also a need for a patellar component that can help lessen anterior knee pain, particularly during deep-flexion activities because the component/bone interface shear force is so high during these activities. There is also a need for a patellar component that can transition during the range of knee movement in a controlled way. There is a further need for a patellar component that has an increased volume of material in certain regions that strengthen the component and help reduce failures.

SUMMARY

Embodiments of the present invention provide patellar components that are shaped to reduce or minimize shear force and accommodate slight implantation error. Further, embodiments may lessen anterior knee pain, particularly during deep-flexion activities and ease the transition during the range of knee movement in a controlled way.

According to an aspect of the present invention, there is provided a patellar component, comprising:
a patella component body having (a) a first surface that engages natural patellar bone in use; and (b) a second surface that bears against a femoral component in use, the second surface having superior, inferior, medial, and lateral edge surfaces, the second surface further comprising:

(i) a substantially axis-symmetric portion extending from the medial edge surface to the lateral edge surface that contacts a femoral component in use;

(ii) one or more facet surfaces extending from the substantially axis-symmetric section, the one or more facet surfaces contacting a femoral component in use.

According to one embodiment the patellar may further comprise one or more reduced portions at the superior edge surface, the inferior edge surface, or both, to allow a smooth transition over a femoral component during flexion and extension.

According to a further embodiment, the substantially axis-symmetric portion contacts a femoral component in a fixed range of motion in use, and the one or more facet surfaces contacts a femoral component outside a fixed range of motion.

According to an even further embodiment, the one or more facet surfaces scoop or extend concavely away from the substantially axis-symmetric portion.

According to another embodiment, the substantially axis-symmetric section comprises pie-shaped slivers that have wider curved portions at the medial and lateral edges, with the slivers meeting at an apex of the substantially axis-symmetric section.

A further embodiment provides a substantially axis-symmetric section that facilitates mal-rotation tolerance in use.

According to a further embodiment, the first surface that engages patellar bone at a patellar bone/patellar component interface, and the second surface provides contact vectors throughout a range of motion that are close to normal to the patellar bone/patella component interface.

According to further embodiments, the contact vectors are from about 0-30 degrees in one embodiment, or 0-20 degrees in another embodiment, or 0-10 degrees in a further embodiment, or 0-5 degrees in an even further embodiment, from one of:

(a) a line that is about perpendicular to the patellar bone/patella component interface for an onset component;

(b) a line that is about parallel to an axis prepared in the patellar bone for an inset component or (c) a line that is about perpendicular to a reference line defined as a line between where a quadriceps muscle tendon attaches to a superior pole of the patella and where a patella tendon attaches to an inferior pole of the patella.

According to a further embodiment, the one or more reduced portions comprise an edge radius.

A further embodiment provides a relieved portion located where an apex of the substantially axis-symmetric portion would otherwise be, wherein the one or more facets extend on outer sides of the substantially axis-symmetric portion.

According to a further embodiment, the one or more facets extend concavely from the substantially axis-symmetric portion.

According to a further embodiment, the relieved portion separates the substantially axis-symmetric portion into a first substantially axis-symmetric portion and a second substantially axis-symmetric portion, wherein the first substantially axis-symmetric portion extends from the medial edge surface of the component to a medial central portion, and the second substantially axis-symmetric portion extends from the lateral edge surface of the component to a lateral central portion. In another embodiment, the relieved portion creates separate contact patches in the facets that contact the femoral component, even in deep flexion in use.

According to another aspect of the invention, there is provided a patellar component, comprising:

a patella component body having (a) a first surface that engages patellar bone in use; and (b) a second surface that bears against a femoral component, the second surface having superior and inferior edge surfaces, the second surface further comprising:

a convex articular surface formed by sweeping a profile about one or more axes, none of which intersect the second surface.

Another embodiment of this aspect may comprise the one or more axes substantially aligned in the medial to lateral direction.

According to a further embodiment, this aspect may also have one or more reduced portions at the superior edge surface, the inferior edge surface, or both, to allow a smooth transition over the femoral component during flexion and extension.

According to a further embodiment, the first surface engages patellar bone at a patellar bone/patellar component interface, and the second surface provides contact vectors throughout a range of motion that are close to normal to the patellar bone/patella component interface.

According to further embodiments, the contact vectors are from about 0-30 degrees in one embodiment, or 0-20 degrees in another embodiment, or 0-10 degrees in a further embodiment, or 0-5 degrees in an even further embodiment, from one of:

(a) a line that is about perpendicular to the patellar bone/patella component interface for an onset component;

(b) a line that is about parallel to an axis prepared in the patellar bone for an inset component or (c) a line that is about perpendicular to a reference line defined as a line between where a quadriceps muscle tendon attaches to a superior pole of the patella and where a patella tendon attaches to an inferior pole of the patella.

In another embodiment 25, the convex articular surface has a radius of curvature between about 50-250 mm.

According to an even further aspect of the invention, there is provided a patellar component characterized that, when in use at angles of knee flexion greater than about 90 degrees, a contact vector angle between the component and a femoral component is from about 0-30 degrees in one embodiment, or 0-20 degrees in another embodiment, or 0-10 degrees in a further embodiment, or 0-5 degrees in an even further embodiment, from one of:

(a) a line that is about perpendicular to a patellar bone/patellar component interface for an onset component;

(b) a line that is about parallel to an axis prepared in the patellar bone for an inset component or (c) a line that is about perpendicular to a reference line defined as a line between where a quadriceps muscle tendon attaches to a superior pole of the patella and where a patella tendon attaches to an inferior pole of the patella.

According to a further aspect of the invention, there is provided a method for implanting a patella component comprising:

(a) providing a femoral component:

(b) providing a patellar component, comprising:

a patella component body having (i) a first surface that engages natural patellar bone in use; and (ii) a second surface that bears against the femoral component in use, the second surface having superior, inferior, medial, and lateral edge surfaces, the second surface further comprising:

(1) a substantially axis-symmetric portion extending from the medial edge surface to the lateral edge surface that contacts a femoral component in use; and (2) one or more facet surfaces extending from the substantially axis-symmetric section, the one or more facet surfaces contacting a femoral component in use;

(c) preparing a recipient's natural patella to receive the implant;

(d) implanting the implant on a portion of the natural patella.

"Embodiment" as used herein can be considered to mean an aspect or an object of the invention, and vice versa.

BRIEF DESCRIPTION OF SEVERAL VIEWS OF THE DRAWINGS

FIG. 11 shows a top perspective view of the patellar component of FIG. 10.

FIG. 12 shows a side plan view in the medial to lateral direction of the patellar component of FIG. 10.

FIG. 13 shows a side plan view in the superior to inferior direction of the patellar component of FIG. 10.

DETAILED DESCRIPTION OF THE INVENTION

Embodiments of the present invention provide patellar prostheses that are designed to form a patella portion that replaces a part of a natural patella. The embodiments may decrease the shear force that is experienced by traditional dome-shaped patellar components, while also providing ease of implantation and accommodating a range of surgical error.

In order to reduce component/bone interface shear forces, which can be a source of pain and component failure, the ideal articular surface for a patellar component has a substantially flat profile. However, in order to increase contact area for better durability, the ideal articular surface substantially matches the coronal and sagittal profile of the trochlear groove of the femoral component. Finally, in order to allow for rotational laxity (surgical error), the ideal articular surface is axis-symmetric (like the button or circular patellar components discussed above). Embodiments of the patellar components described are an appropriate and optimal mix of these concepts. More specifically, the closer that the design is to a button design, the less the constraint differences between the trochlear groove articulation area and the intracondylar articulation area will affect rotational problems of the component, but the bone/patella interface shear forces will almost likely be increased in undesirable ways. However, the closer the geometry is to an "anatomic" design, the interface forces can be reduced (or oriented in a more desirable direction), but the design can be sensitive to the constraint difference and the inevitable surgical mal-rotations. Embodiments of the described designs are intended to arrange the articular surfaces of the patella such that, even with certain amounts of rotation, the contact vectors remain generally normal to the component/bone interface, thus causing the shear forces to be low. For example, at 90 degrees of flexion or greater, embodiments may reduce the contact vectors to 0-50 degrees in one embodiment, 0-45 degrees in another embodiment, 0-40 degrees in a further embodiment, 0-35 degrees in another embodiment, 0-30 degrees in another embodiment, 0-25 degrees in another embodiment, 0-20 degrees in a further embodiment, 0-15 degrees in another embodiment, 0-10 degrees in another embodiment, and about 0-5 degrees in a further embodiment, from one of either (a) a line that is about perpendicular to the patellar bone/patella component interface for an onset component or (b) a line that is about parallel to an axis prepared in the patellar bone for an inset component, or (c) the alternate reference frames described below.

Figure 18:
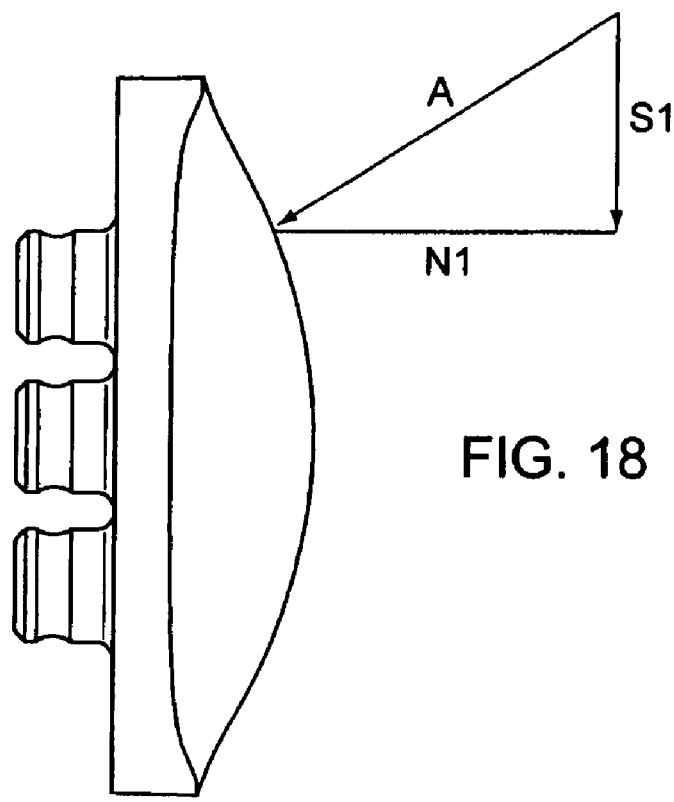
FIG. 18 shows an example of shear forces experienced by a button or dome patellar component.
Figure 19:
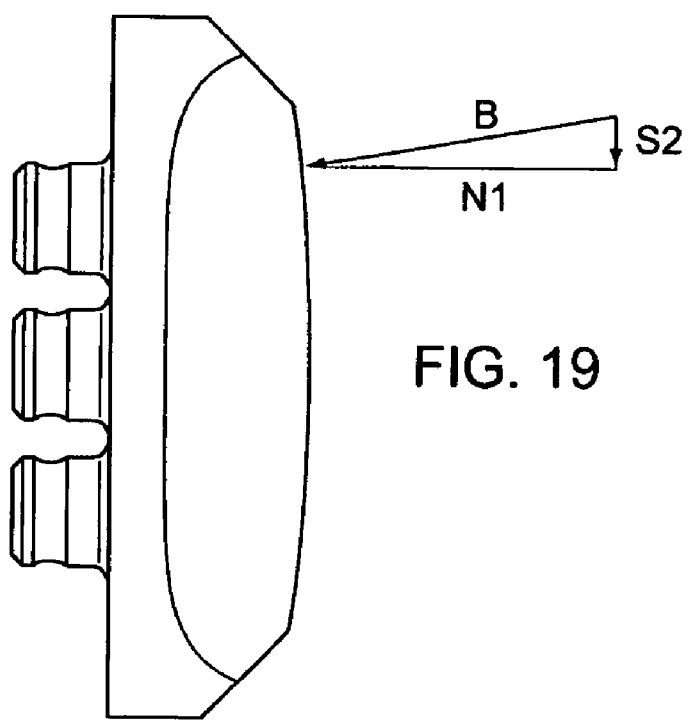
FIG. 19 shows an example of shear forces experienced by the patellar component of FIG. 16.

For (a): the line that is perpendicular to the patellar bone/patella component interface, an example for one embodiment is shown in FIGS. 18 and 19. A perpendicular line is shown by N, which represents the "normal force component." (N1 is shown is in FIG. 18 and N2 is shown in FIG. 19.) For (b): the line that is about parallel to an axis prepared in the patellar bone, an example is the axis formed by a drill when preparing a recess in the bone to receive an inset patellar component. The axis of the drill is also the axis prepared in the patellar bone.

Figure 23:
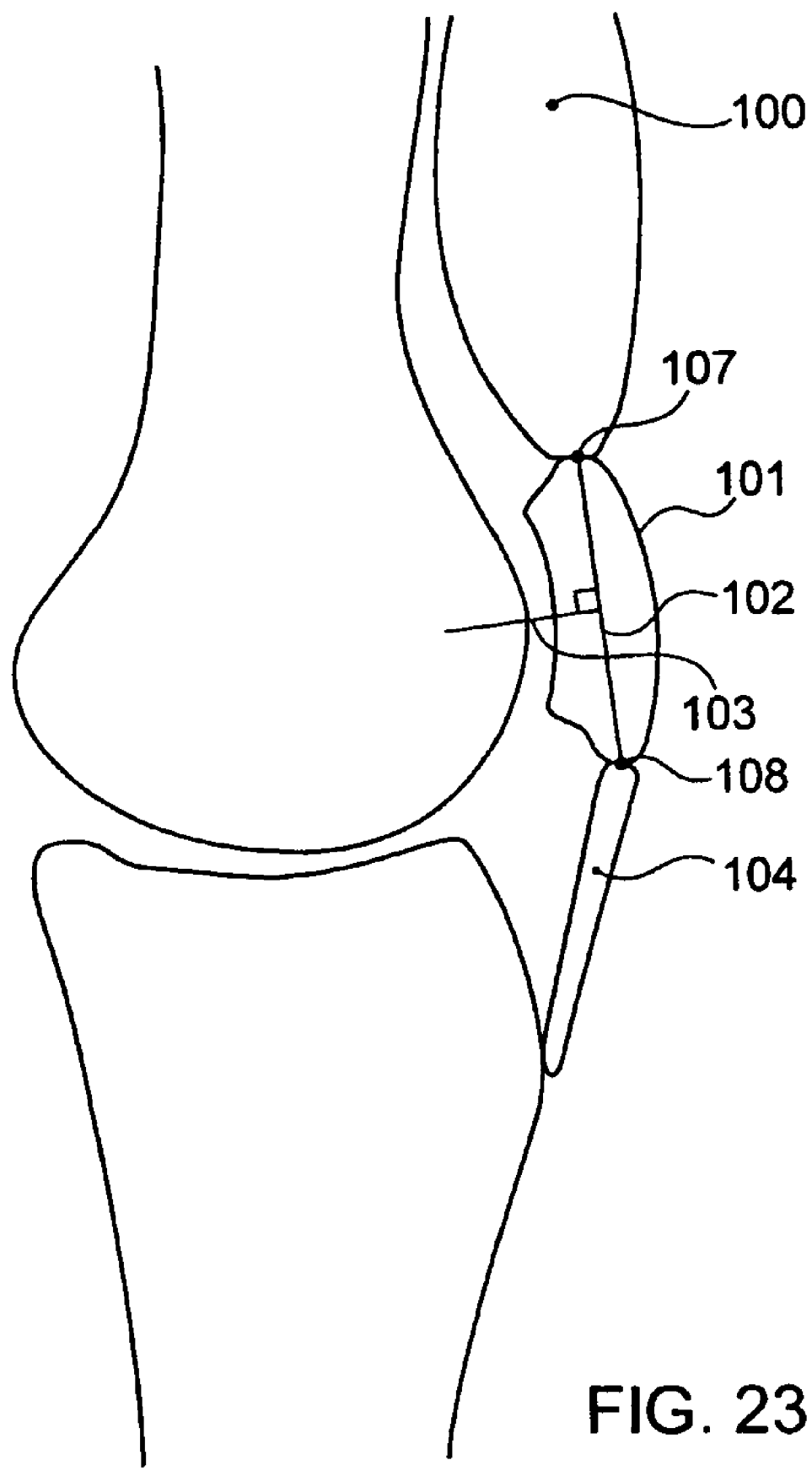
FIG. 23 shows an example of an alternate reference frame that can be used to measure the normal force component, contact force vectors, and shear force components.

An alternate way to measure the angle between the contact vector and a normal direction on the patella is shown in FIG. 23. This alternate way uses a different reference line—one that is not defined by the placement of the patellar component, but is instead defined by an anatomic reference frame. In this option, the two areas of interest are (1) the attachment area 107 where the quadriceps muscle tendon 100 attaches to the superior pole of the patella 101 (first attachment area) and (2) the attachment area 108 where the patella tendon 104 attaches to the inferior pole of the patella (second attachment area). These are the areas where forces extend through the patella.

If a line 102 is drawn from an area within each attachment area 107 and 108 (preferably the center area of each area, but that is not required), line 102 can be used as a reference line. When viewed from the medial/lateral direction, this reference line can be used to define a reference from which the contact forces acting on the patella can be measured. For example, a contact force angle can be measured from line 103, which is perpendicular to reference line 102.

Figure 1:
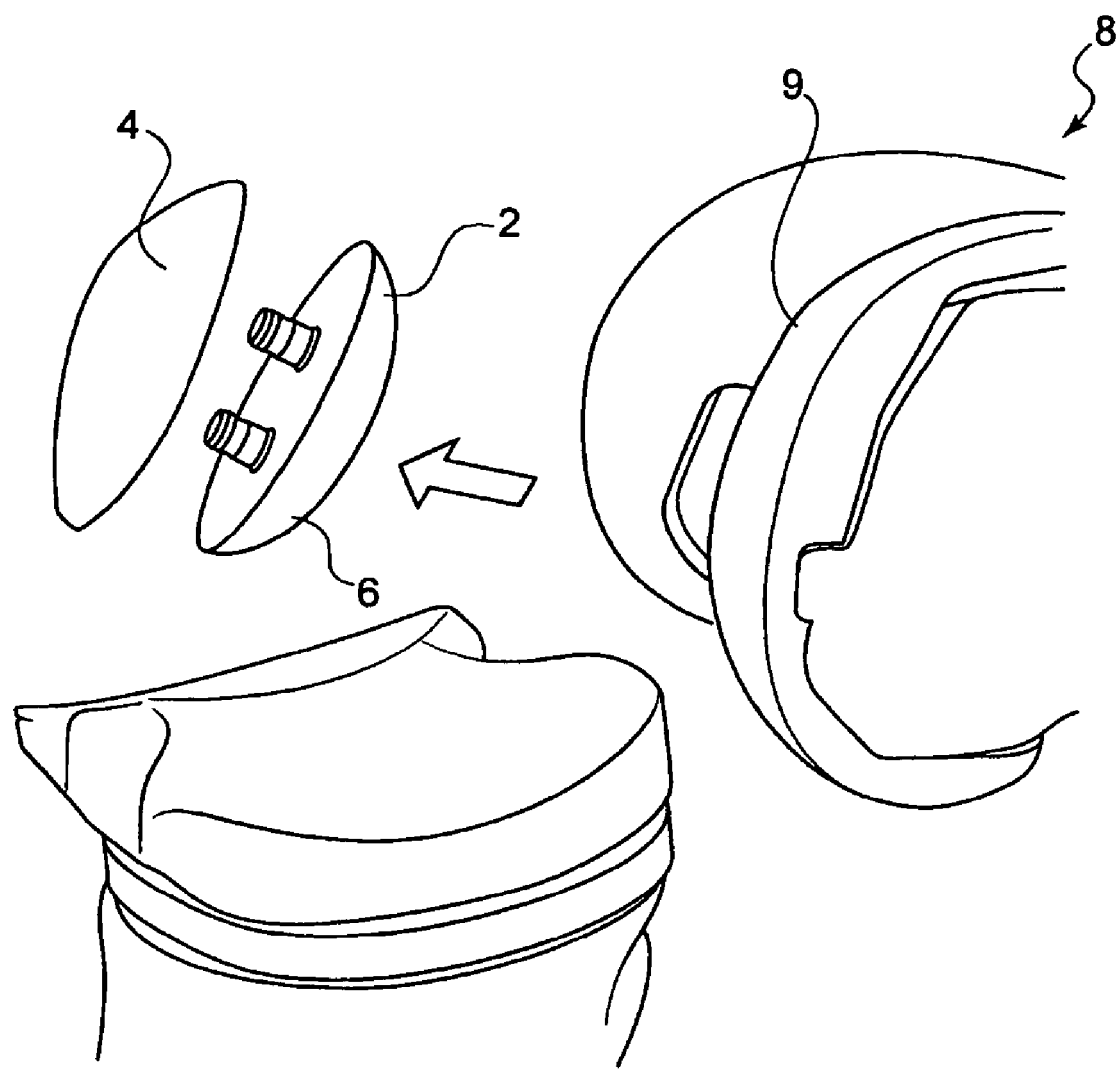
FIG. 1 shows a side perspective view of how a patellar component may be secured to a portion of a natural patella.
Figure 2:
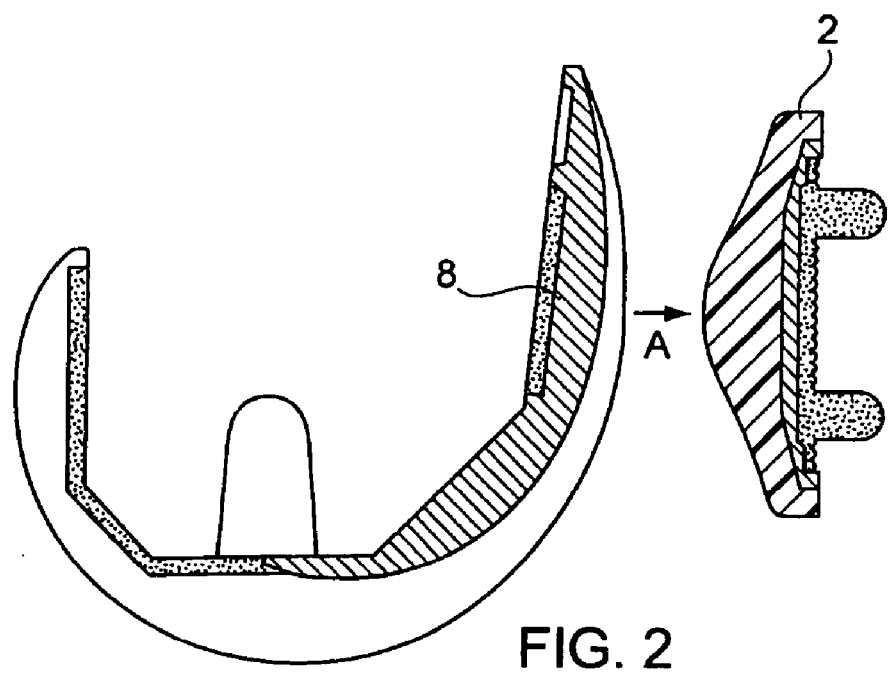
FIG. 2 shows an example of the compressive force that a femoral component exerts on a button or domed patellar component when a knee is in extension.
Figure 3:
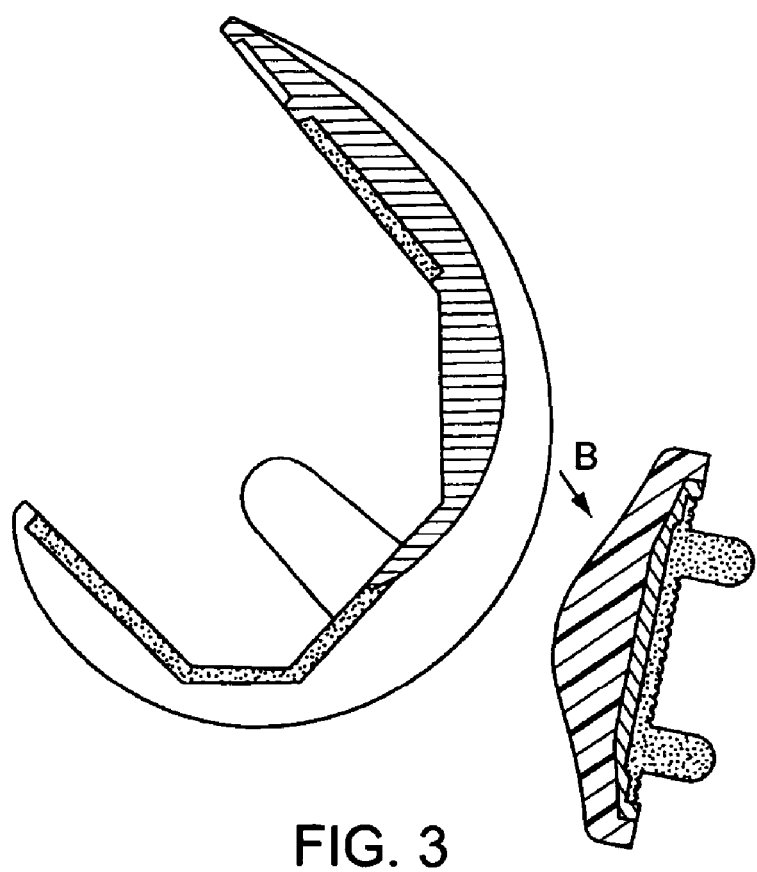
FIG. 3 shows an example of the shear force that a femoral component exerts on a button or domed patellar component when a knee is in flexion.
Figure 4:
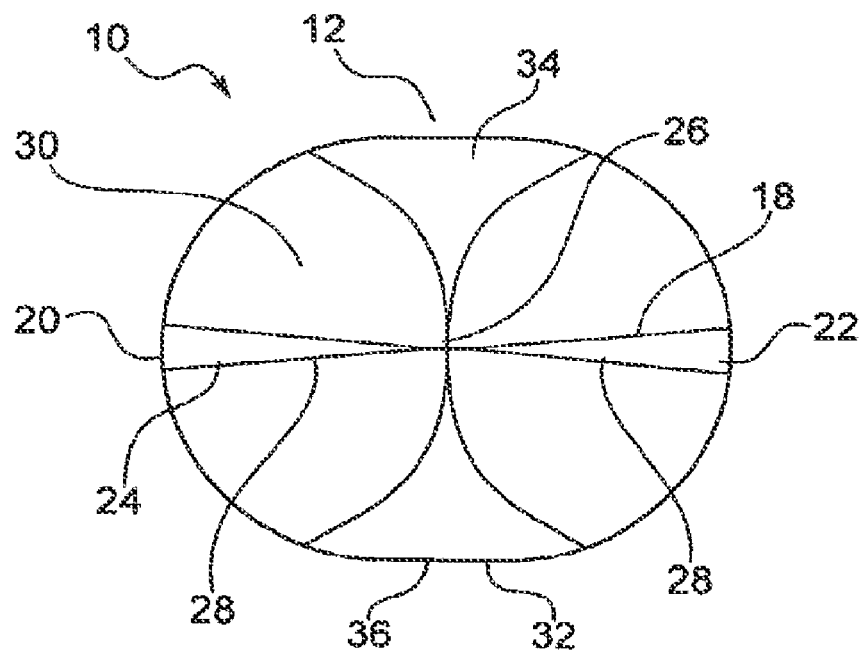
FIG. 4 shows a top plan view of a patellar component according to an embodiment of the invention.
Figure 5:
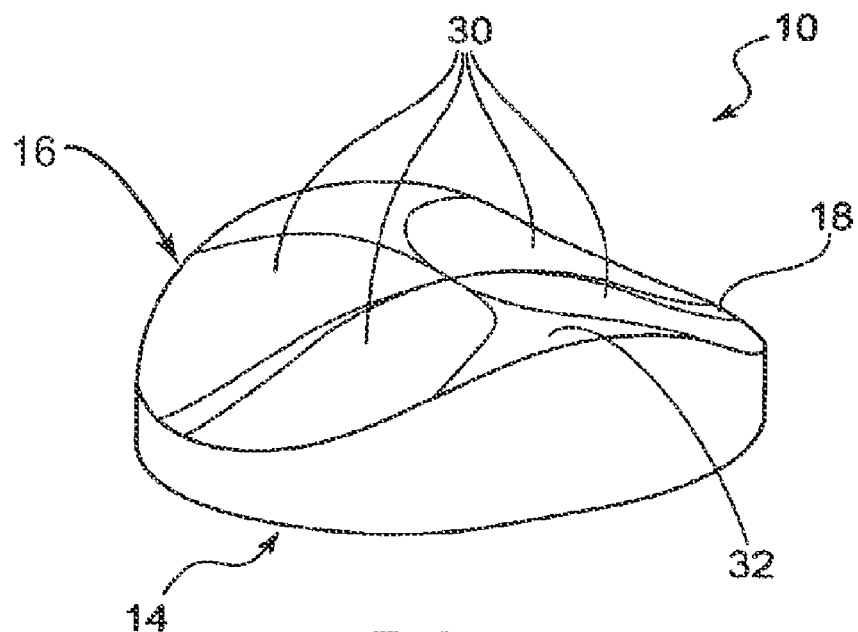
FIG. 5 shows a top perspective view of the patellar component of FIG. 4.
Figure 6:
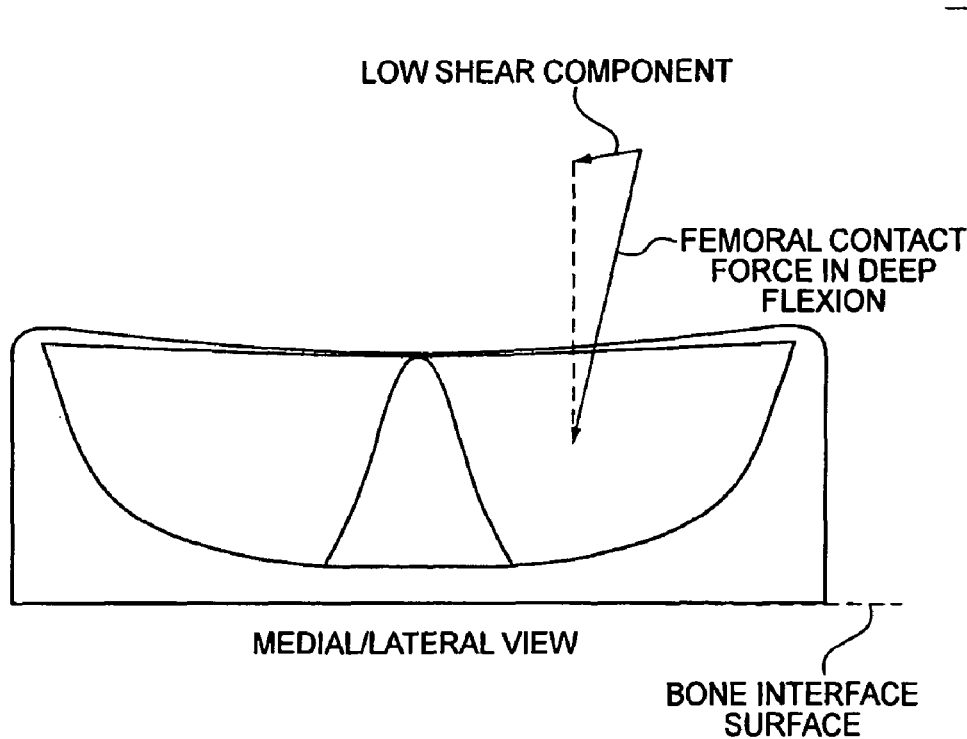
FIG. 6 shows a side plan view in the medial to lateral direction of the patellar component of FIG. 4.
Figure 6:
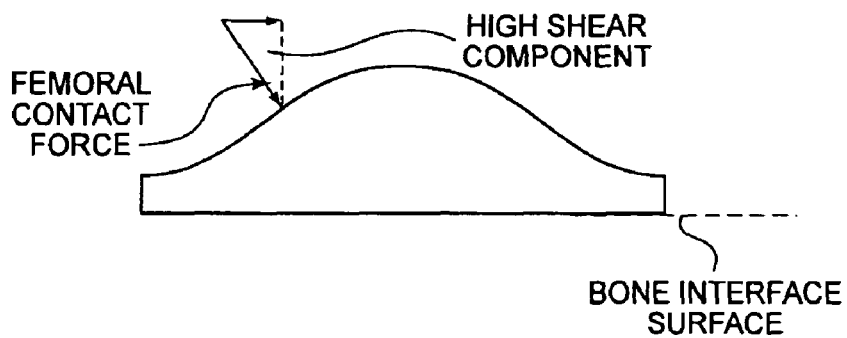

Referring now to the patellar components themselves, in a first embodiment, shown in FIGS. 4-6, the patellar component 10 has an component body 12, a first surface 14 that engages patellar bone, and a second surface 16 that bears against a femoral component. The first surface 14 is typically flat with one or more pegs (not shown) that secure the component 10 to a patient's natural patella that has been prepared to receive the component 10. As discussed above, embodiments of the invention may be inset or onset components. Any appropriate number of pegs and orientation of pegs may be used, and any other appropriate securing mechanism may be used instead of, or in addition to, pegs.

Second surface 16 is the surface that articulates with a femoral component and determines to what extent forces will act on the first surface 14/bone interface. Second surface 16 is formed from a set of articular surfaces that are divided into substantially axis-symmetric regions, faceted regions, and blended regions. The combination of these surfaces lessens shear forces at the component/bone interface, as well as allows for mal-rotation implantation tolerance.

Second surface 16 is shown having a substantially axis-symmetric portion 18 that extends from a medial edge surface 20 to a lateral edge surface 22 of component 10. The substantially axis-symmetric portion 18 has a curved radius over a portion of the component 10. In one embodiment, curved portions 24 near the medial 20 and lateral edges 22 are somewhat wider than the curved portion at the apex 26 of the component. This creates, in essence, two thins slivers 28 (or "pie-shaped" slivers) that form the sides of substantially axis-symmetric portion 18. These slivers 28 articulate against a femoral component in a fixed range of motion, and help provide the benefits that are obtained when using a completely axis-symmetric (i.e., button) patella. (Note: axis-symmetric portion 18 is referred to as "substantially" axis-symmetric, because, as discussed below, the portion need not be exactly symmetric in order to function. Alternate surface geometries, such a free forming surfaces, may achieve a similar effect and are discussed below.)

Within a fixed range of rotation, the patellar component 10 contacts the femoral component on the substantially axis-symmetric portions 18. After a threshold value of rotation is reached (which may be any threshold level, examples of which may be between 5-30 degrees, 5-15 degrees, or even more specifically 5-10 degrees, or any other appropriate range), the contact between component 10 and femoral component typically moves into faceted surfaces 30, where a more conforming contact condition exists. For example, as the knee flexes and the patella transitions between the trochlear groove and the intracondylar area, the contact may move from the slivers 28 to the facet surfaces 30.

Figure 22:
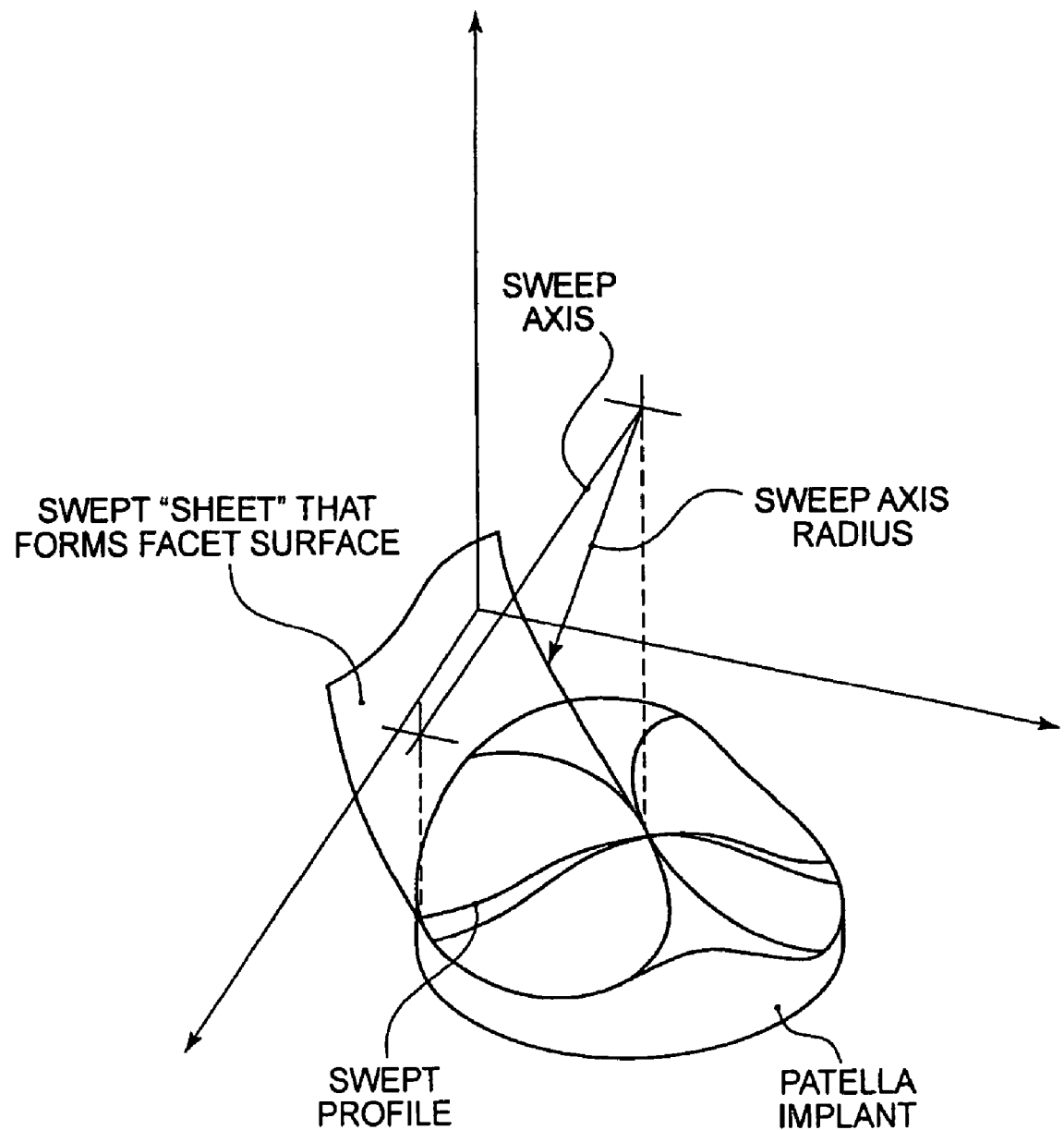
FIG. 22 shows an example of a geometry construction that may be used to design the component of FIGS. 4-6.

As shown in FIG. 5, facet surfaces 30 are provided on the sides of substantially axis-symmetric portion 18. Facet surfaces 30 define indentations that "scoop" or extend down and concavely away from slivers 28 of substantially axis-symmetric portion 18. In the embodiment shown, there are four facet surfaces 30, one in each quadrant defined by the medial to lateral substantially axis-symmetric portion 18. For perspective and comparison to the button (dome-shaped) implants described above, consider a dome-shaped component that has been shaved to maintain a sliver of a substantially axis-symmetric portion in the medial to lateral direction. Facet surfaces 30 may be any depth that allows facet surfaces 30 to cooperate with the profile of the femoral component condyles. One way in which the geometry of facet surfaces 30 may be defined is shown in FIG. 22. The edge of a substantially axis-symmetric portion can be identified and "extruded" about an axis in space above the articulating surface. This "extruded" surface or "swept sheet" can define a depth range for facet surfaces 30. Surfaces 30 typically contact the femoral component outside a fixed range of motion, i.e., when the contact moves from the substantially axis-symmetric portions 18 to the more conforming facet surfaces 30.

When a person in whom patellar component 10 is positioned is standing upright, the normal line of pressure is directed at or near the apex 26 of the substantially axis-symmetric portion 18. As the person flexes the knee (e.g., begins to initiate a squatting position), the patellar component rotates in relation to the femoral component such that the facet surfaces 30 are now the area upon which contact is made. Facet surfaces 30 may provide a platform that cooperates with the femoral component and more closely approximates a natural patella. Facets 30 provide an increased level of conformity with the femoral component at increased levels of mal-rotation. As shown in FIG. 6, the shear force component is lessened when the contact surface is a facet surface 30.

The transition between the substantially axis-symmetric sliver 28 and the facet surface 30 on each side of sliver 28 is preferably smooth or blended, in order to prevent a shift or clunk during the flexion transition. Also shown in FIGS. 4-6, component 10 may be provided with reduced portions 32 at the superior edge surface 34 and the inferior edge surface 36. Reduced portions 32 are provided in order to avoid "clunk" or other interference in the trochlear groove that occurs during transition between flexion and extension.

Figure 7:
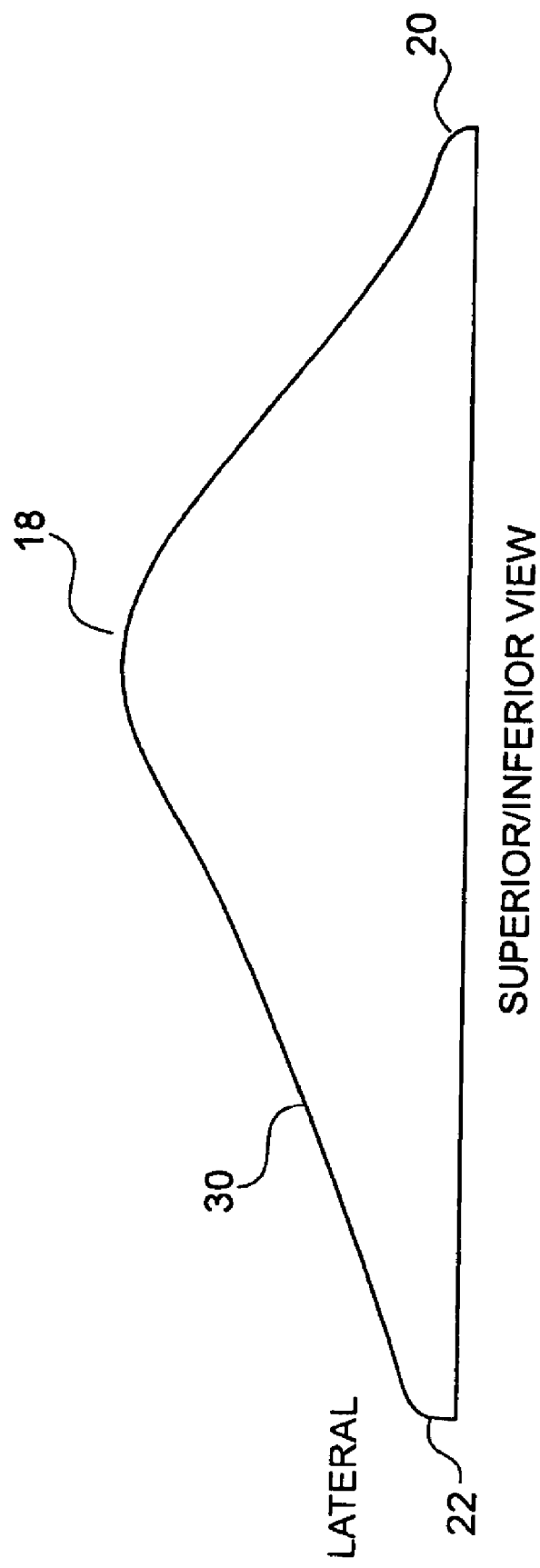
FIG. 7 shows a side plan view in the superior to inferior direction of an alternate embodiment of a patellar component with a medialized apex.
Figure 8:
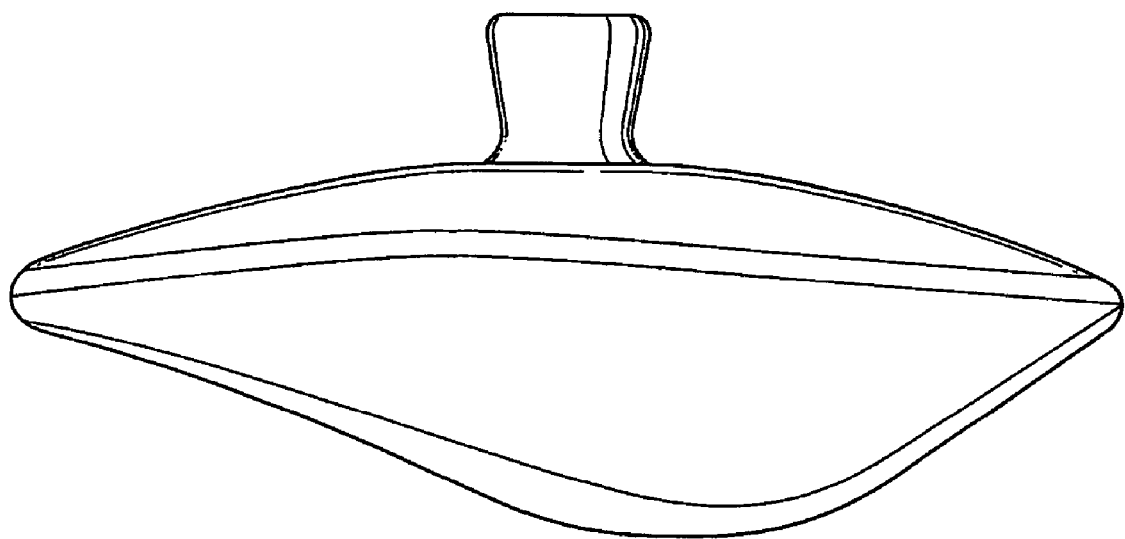
FIG. 8 shows a superior to inferior view of a component when implanted on a patella bone in full extension. This component has a design similar to that shown in FIG. 7, although this implant is attached by an inlay (insert) method.

FIG. 7 shows an alternate component 10 from the superior/inferior direction. In this embodiment, it can be seen that substantially axis-symmetric portion 18 may be positioned more to the medial edge 20 of the component (or medially biased). FIG. 8 shows the implant of FIG. 7 in an inferior to superior direction when implanted on a patient's left knee. This figure also shows how a component may be designed as an inlay design (e.g., so that it can be inset, as opposed to onset). Again, the apex of implant (or in this case, the substantially axis-symmetric portion) may be medialized to provide rotational laxity axes that are not centered on the patella, such as the medial biased axis shown in FIG. 8.

As discussed briefly above, it should be understood that other articular surface geometries can be used in order to achieve similar effects as those provided by the substantially axis-symmetric portion 18 and facet surfaces 30. For example, component 10 could be provided with free-form shapes that approximate a geometry that is similar to the discrete surfaces that have been described. The free-form shapes need not be precise. For example, an axis-symmetric portion or substantially axis-symmetric portion need not be perfectly symmetric or a faceted surface could be more or less indented than other faceted surfaces or designed so that other contact conditions exist.

Figure 9:
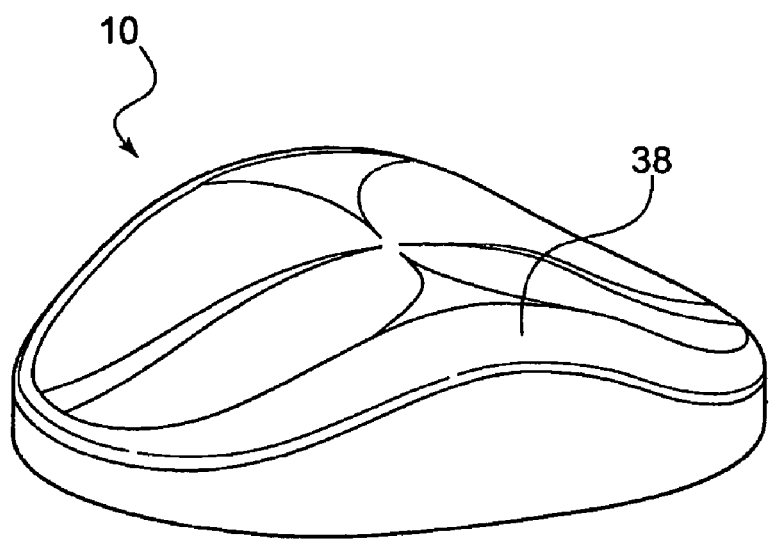
FIG. 9 shows a side perspective view of a component having an increased edge radius.

FIG. 9 shows a component that has a greater edge radius than that shown by reduced portions 32 of FIGS. 4-6. Edge radius 38 in FIG. 9 has even more material removed from reduced portion 32, which again, may help avoid clunk or other interference in the trochlear groove that occurs during transition between flexion and extension. This example is shown to illustrate that reduced portions 32 may be slight or they may have a pronounced edge radius 38.

Another embodiment of a patellar component 50 is shown in FIGS. 10-13. This embodiment has many of the above-described features, but it also includes a relieved portion 52 in the superior to inferior direction (in some embodiments, it extends from the superior edge surface 34 to the inferior edge surface 36). As shown in FIG. 11, relieved portion 52 divides central area 56 of surface 16 into two portions (e.g., into medial and lateral sides). Relieved portion 52 may be concave, flat, substantially flat, or slightly convex. Its general purpose is to provide a divider with reduced contact area such that minimal to no contact between the relieved portion 52 and the patellar groove of the femoral component occurs. This design provides an arrangement of the articular surfaces such that a constant constraint pattern exists with the femoral component throughout the available range of motion.

Relieved portion 52 is, in essence, material removed in the apex region of component 10 in order to provide two contact patches 60 all the way through flexion (or substantially all the way through flexions). The manufacture of relieved portion 52 can be referred to as apex-relief. (This concept is similar to a tibial insert that has two patches that maintain contact with a femoral component during flexion.) The patches 60 preferably remain at a relatively constant medial-lateral distance from each other during flexion so that the constraint patterns stay similar. This helps maintain a constant constraint throughout the flexion range on the anterior flange and intracondylar areas of the femoral component. The relieved portion 52 rides along the trochlear groove without making contact. The amount of apex relief provided on component 50 can vary, depending upon the desired design. An increased portion of apex relief may also be provided at the superior-most and inferior-most surfaces (34 and 36) in order to help prevent the "clunk" problems described above. These increased apex relief portions are essentially the above-described reduced portions 32, they are just optionally provided in a more pronounced fashion. Also shown in FIGS. 10-13 are substantially axis-symmetric portion 18, facet surfaces 30, and reduced portions 32 (which may have a slight or a large edge radius). These surfaces may be formed as previously described. In other embodiments, these surfaces may not be present as the dual contact patches may allow for proper force balancing to reduce shear forces and controlled transition.

Figure 10:
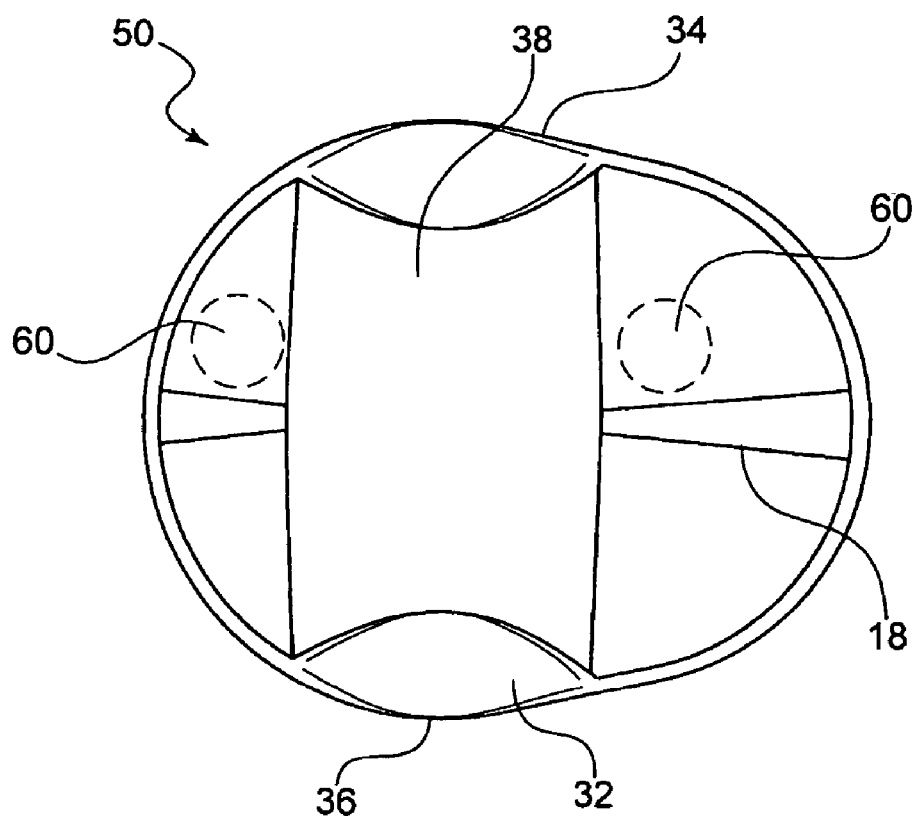
FIG. 10 shows a top plan view of a patellar component according to another embodiment of the invention.
Figure 14:
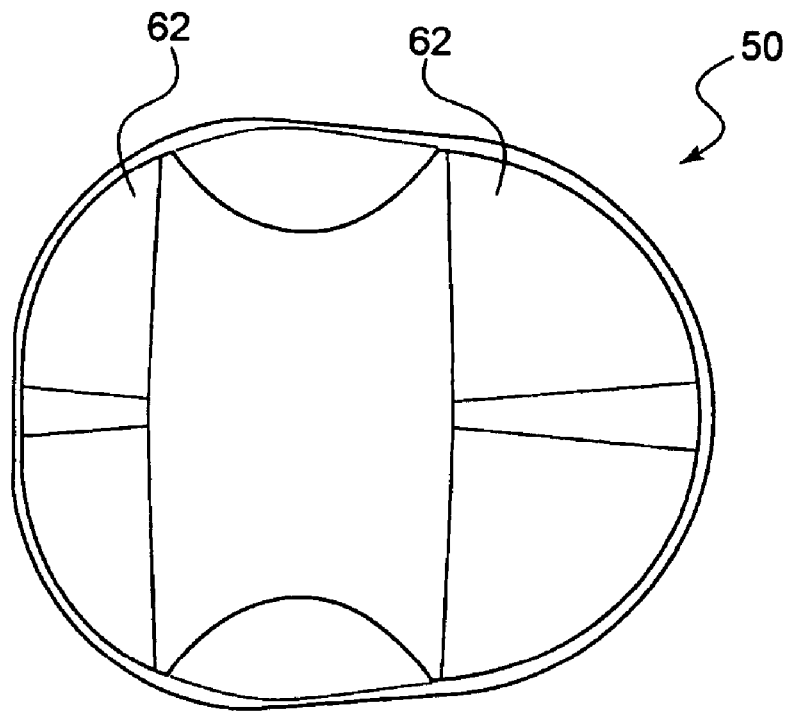
FIG. 14 shows an alternate embodiment of a component having an increased surface area on the articulation surface.

In the alternate embodiment shown in FIG. 14, the profile of the component 50 may be modified to maximize contact area in deeper flexion. Facet surfaces are articulated similar to the implant of FIGS. 4-6, and similar to those implants, the articulate facet surfaces help to reduce shear stresses. Additionally, the medial apex relief edge may be modified to increase the medial contact area in early flexion. For example, as shown in FIG. 14, all axes and dimensions may remain the same as the design shown in FIG. 10, but the contact patches at the upper parts 62 of implant 50 can be slightly modified so that there is a greater articulation surface. In other words, if FIG. 10 is superimposed over FIG. 14, it would be seen that the upper parts 62 provide larger corners or have an extended profile that provide more articulation surface at upper parts 62.

Figure 15:
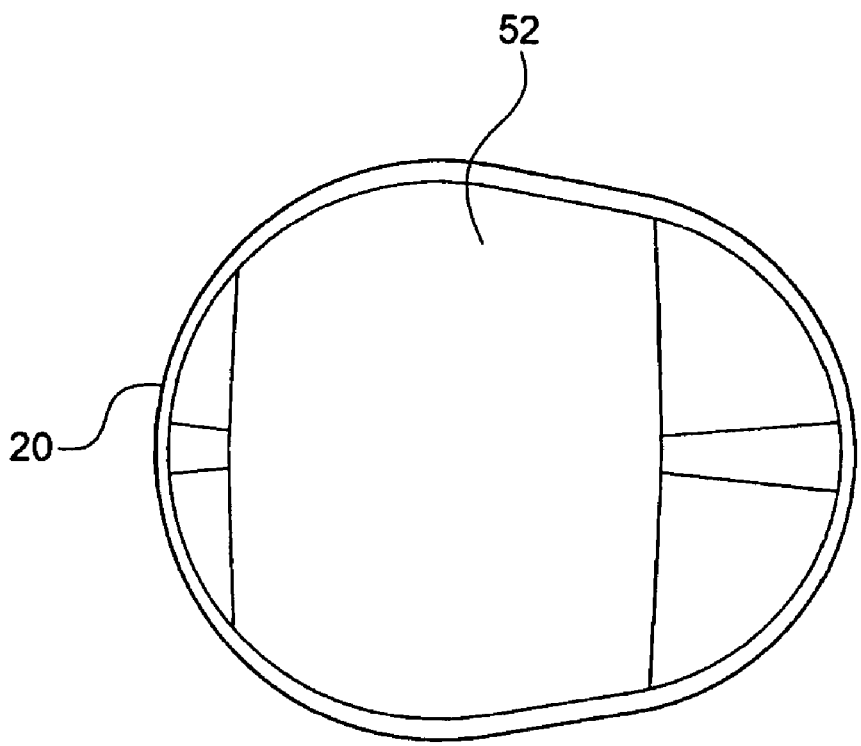
FIG. 15 shows a top plan view of an alternate embodiment of a component having an enlarged relieved portion.

In a further embodiment shown in FIG. 15, the relieved portion 52 may be widened and extend more to the medial 20 and lateral edges 22 (although it extends more to the medial edge side 20 in the embodiment shown). This embodiment does not have a relieved portion 52 that is flat or substantially flat, but is instead slight convex. As discussed, this can still be considered a relieved portion 52 within the scope of this invention. This design may find particular use in connection with a cruciate retaining procedure. The width of relieved portion 52 may be the same as the distance between the condyles of the femoral component. Providing an increased relieved portion minimizes the contact area, but may be necessary in some instances. Although not shown, the relieved portion 52 may also be narrower than in the examples shown. This can maximize contact area, but may sacrifice sensitivity to mal-implantation. An appropriate balance for the necessary procedure can be achieved by combining various aspects of the designs described, depending upon the needs of the patient.

Figure 16:
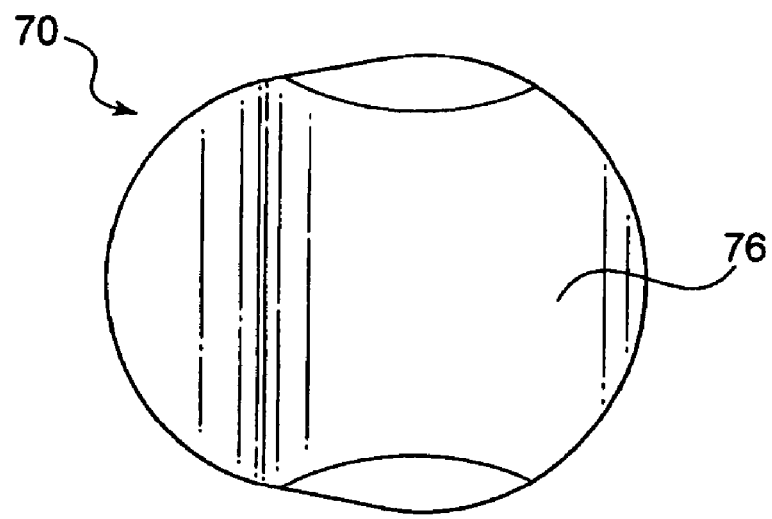
FIG. 16 shows a top plan view of a patellar component according to a further embodiment of the invention.
Figure 17:
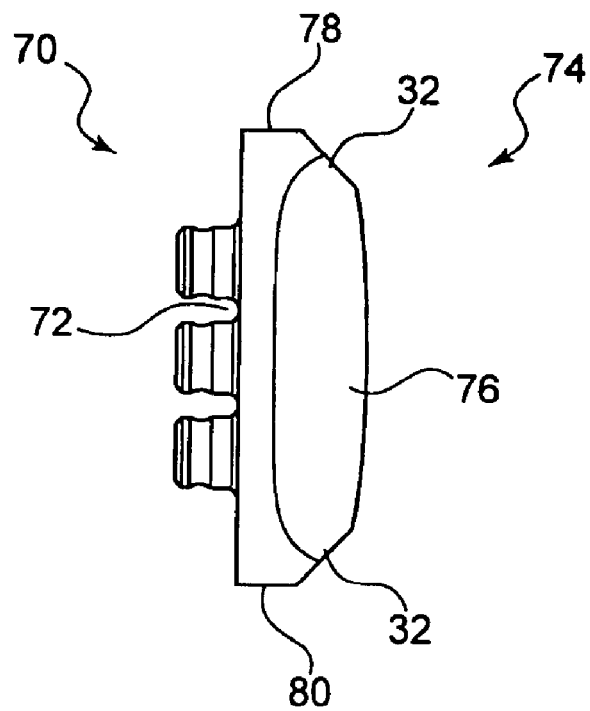
FIG. 17 shows a side plan view in the medial to lateral direction of the patellar component of FIG. 16.
Figure 20:
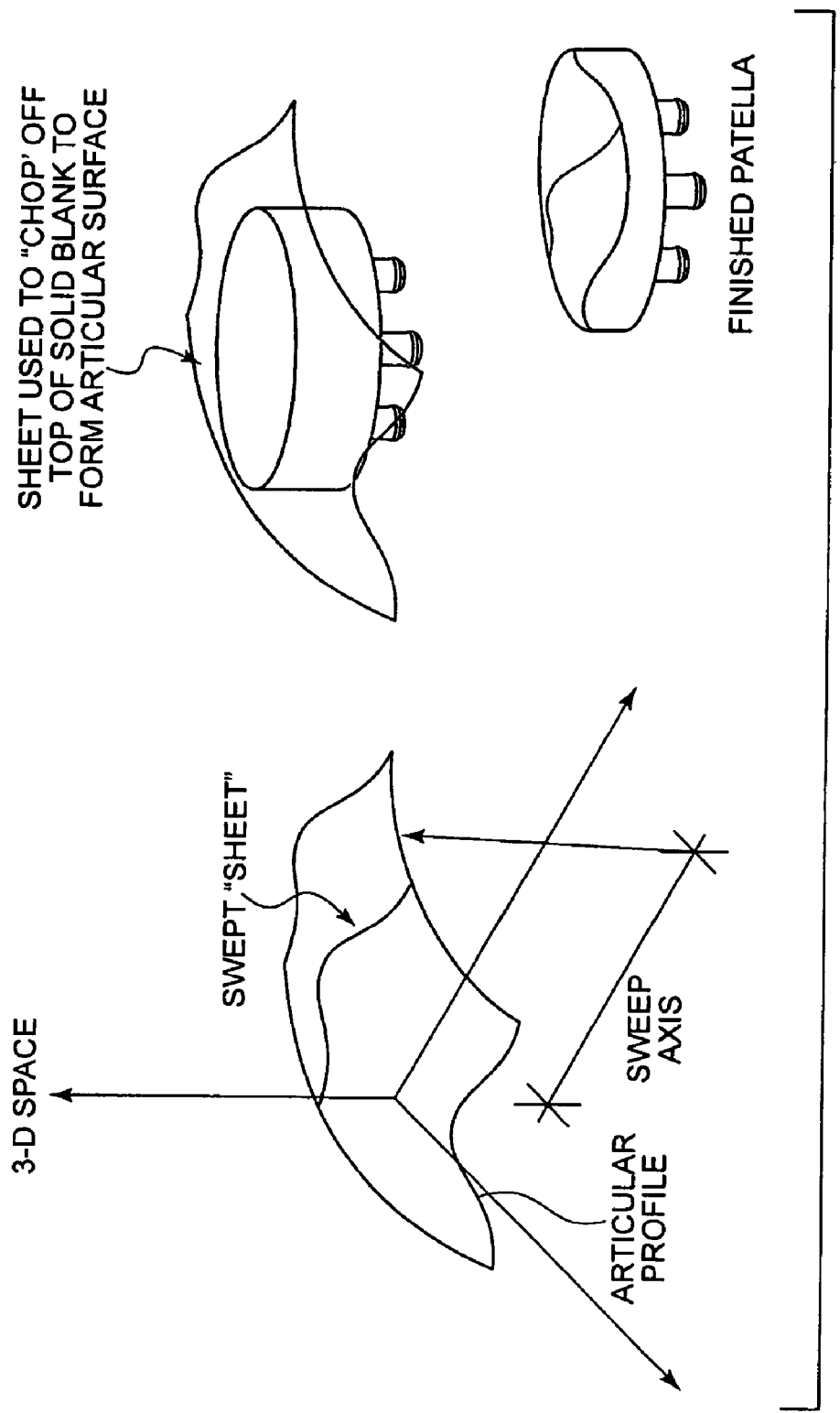
FIG. 20 shows an example of a component geometry construction that may be used to design the component of FIG. 16.

A further embodiment according to further aspects of the invention provides a convex oval patella component 70. Convex patella component 70 is shown in FIGS. 16 and 17 as having an oval shape, although any appropriate shape is within the scope of this invention. Component 70 of this embodiment has a first surface 72 that engages patellar bone and a second surface 74 that articulates against a femoral component. First surface 72 may have features that are similar to the first surface embodiments described above. Second surface 74 is formed having a convex articular surface 76. Surface 76 defines a line with an arc that has been swept about an axis, i.e., a swept arc. An example of the geometry that can be used to construct a convex oval patella component is shown in FIG. 20. In this example, a sweep axis is defined in one plane, and an articular surface profile is swept or "extruded" about the sweep axis. This "extruded surface" or "swept sheet" can be used to define an articular surface 76 of component 70. The articular surface 76 may be formed by sweeping a profile about one or more axes, none of which intersect the second surface. (This is distinguished from the typical methods that are used to design a button or dome patella, illustrated in FIG. 21.) The radius of the convex arc or swept profile can range from about 50-250 mm, with a particularly useful radius at 100 mm. Moreover, the convex articular surface 76 may be made up of multiple axes; for example, the center region could be a different radius than the superior and inferior regions to alter the amount of mal-rotation sensitivity for different flexion angles.

Figure 21:
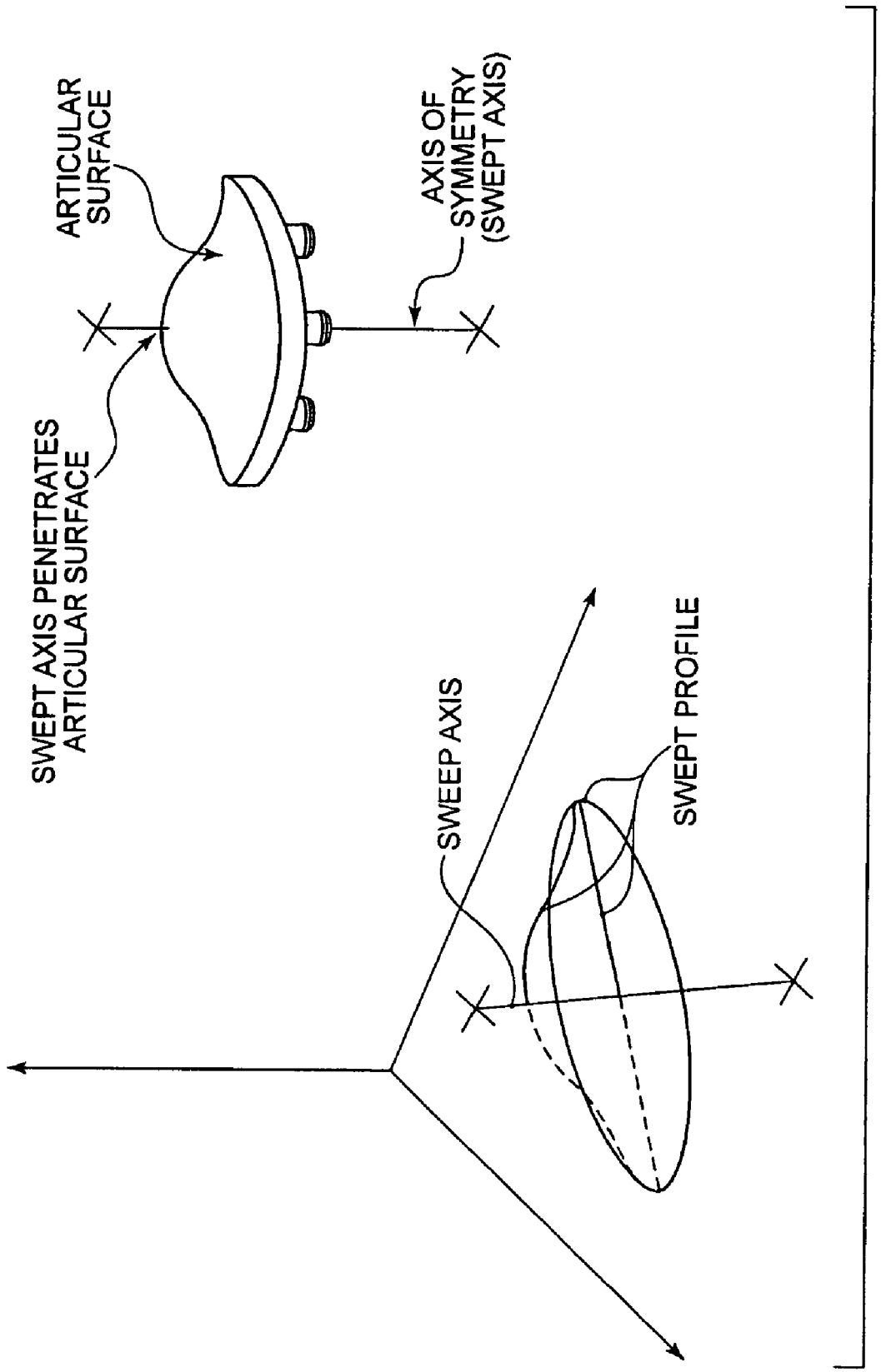
FIG. 21 shows an example of a geometry construction that is used to design a dome or button patellar component of the prior art.

As reflected in the above and in FIG. 22, a patellar implant according to some embodiments may include a patellar component body that includes a central axis that generally extends in an anterior-posterior direction, a first surface configured to bear against a patella, and a second surface configured to bear against a femoral component. In some embodiments, the second surface includes superior, inferior, medial, and lateral edges. As shown in FIG. 22, the second surface further includes at least one axis symmetric articulating surface extending between the medial edge surface to the lateral edge surface, the at least one axis symmetric articulating surface being defined by a plurality of line segments that are oriented to extend outwardly from the central axis. These plurality of line segments of the at least one axis symmetric surface define curved line segments that are substantially the same within that surface (as also reflected by the embodiment of FIG. 21 showing the formation of an axis symmetric surface by sweeping the "swept profile" of FIG. 21 about the "sweep axis" of FIG. 21). In this way, the axis symmetric articulating surface is rotationally symmetric about the central axis. Moreover, as shown in FIG. 22, the at least one facet articulating surface is located superior to the axis symmetric articulating surface and the at least one facet articulating surface is defined by a plurality of line segments that are oriented to extend outwardly from the central axis, the plurality of line segments of the at least one facet articulating surface defining line segments that are not substantially the same within that surface (as illustrated in this particular embodiment by the formation of the facet surface in FIG. 22 by sweeping the "swept profile" of FIG. 22 about the "sweep axis" of FIG. 22). In this way, the facet articulating surface is not rotationally symmetric about the central axis (illustrated by the dashed line). As further shown, the axis symmetric and facet articulating surfaces generally extend in the superior-inferior direction and the medial-lateral direction.

Because a certain trochlear geometry is needed, component 70 may be designed by taking a transverse section of the femoral trochlear groove and sweeping or extruding it about a substantially medial-lateral axis anterior to (opposite the side of) the articular surface of the patella, creating a convex articular surface when sectioned about sagittal planes. When a large convex radius is used, the backside interface shear forces/stresses can be greatly reduced. Since the articular surface is not concave or flat, the sensitivity to mal-rotation (spin) is reduced.

An example comparing the shear forces experienced by a dome or button component to the shear forces experienced by a convex oval patella component 70 is shown in FIGS. 18 and 19. A contact vector for each design is shown with arrows "A" and "B". This is the direction at which forces from a femoral component extend. The normal force component (measured either from the bone/component interface or using the anatomical reference frame defined by FIG. 23) is represented by N (N1 for FIG. 18 and N2 for FIG. 19). The distance between the ends of the contact force vector (A or B) and the normal force component (N1 or N2) is the shear force component, represented by S1 and S2. FIG. 18 shows the shear force "S1" on a dome/button component, and FIG. 19 shows the shear force "S2" on a convex oval component 70. The contact force "B" on the convex oval component is much closer to normal to the first surface, which means that shear forces are greatly reduced with this design. In short, by changing the convex radius, shear force reduction and mal-rotation sensitivity can be balanced. This design is also more optimal than concave or flat designs for femoral trochlear grooves that are not straight or that are slightly arcuate.

Referring back to FIG. 17, a superior edge surface 78 and inferior edge surface 80 may also have reduced portions 32. As discussed above, reduced portions 32 can help the transition of the component 70 between the trochlear groove and the condyles, preventing a catch or a clunk that may occur when transitioning between flexion and extension. This example also shows that reduced portions may be rounded or angular. The basic purpose in all embodiments discussed is simply to remove material from the edges of the component. The convex component 70 design may also include a greater volume of material than the dome/button patella designs described, as shown in the comparison between FIGS. 18 and 19. The portion at which arrow "B" points in FIG. 19 has more material, and is thus more durable in that region, than the portion at which arrow "A" in FIG. 18 points. In short, the convex oval patella design can be useful to prevent excessive wear or fracture in certain regions.

The patellar component embodiments described herein may be implanted using traditional surgical techniques. For example, the patella is traditionally prepared after the tibial and femoral cuts have been made, but prior to trial placement. Once the appropriate patellar component is selected, the patella should be reamed at the appropriate depth and location. (Different reaming equipment and techniques will be used depending upon whether the implant will be onset or inset, as is understood in the art.) The overall thickness of the patella should be measured in order to determine the amount of bone that remains after cutting, and then the patella is resected or resurfaced. A patella peg drill can then be used to drill peg holes. Then once a portion of the natural patella is prepared, the appropriate patellar component is implanted.

Changes and modifications, additions and deletions may be made to the structures and methods recited above and shown in the drawings without departing from the scope or spirit of the invention and the following claims.

What is claimed is:

1. A patellar implant comprising:
a patellar component body comprising:
  a central axis that generally extends in an anterior-posterior direction;
  a first surface configured to bear against a patella;
  a second surface configured to bear against a femoral component, the second surface comprising a superior edge, an inferior edge, a medial edge, and a lateral edge, the second surface further comprising:
    at least one axis symmetric articulating surface extending between the medial edge surface and the lateral edge, wherein the at least one axis symmetric articulating surface is defined by a plurality of line segments that are oriented to extend outwardly from the central axis, the plurality of line segments of the at least one axis symmetric surface defining curved line segments that are substantially the same within that surface;
    at least one facet articulating surface located superior to the axis symmetric articulating surface, wherein the at least one facet articulating surface is defined by a plurality of line segments that are oriented to extend outwardly from the central axis, the plurality of line segments of the at least one facet articulating surface defining line segments that are not substantially the same within that surface, and
  wherein the axis symmetric and facet articulating surfaces generally extend in a superior-inferior direction and a medial-lateral direction.

2. The patellar implant of claim 1, wherein the at least one facet articulating surface is axis symmetric about a second axis.

3. The patellar implant of claim 2, wherein the second axis extends generally in the medial-lateral direction and is positioned posterior of the patellar implant.

4. The patellar implant of claim 1, wherein the central axis is generally perpendicular to a plane extending in the superior-inferior direction and the medial-lateral direction.

5. The patellar implant of claim 1, wherein the plurality of line segments of the at least one axis symmetric articulating surface are substantially the same when viewed in a plurality of planes, each plane containing the central axis and one of the line segments of the at least one axis symmetric articulating surface.

6. The patellar implant of claim 1, wherein the at least one facet articulating surface comprises four facet articulating surfaces.

7. The patellar implant of claim 6, wherein two of the four facet articulating surfaces are positioned superior of the at least one axis symmetric articulating surface and the other two of the four facet articulating surfaces are positioned inferior of the at least one axis symmetric articulating surface.

8. The patellar implant of claim 7, wherein the at least one axis symmetric articulating surface defines two axis symmetric articulating surfaces, each axis symmetric articulating surface defining an approximately wedge-shaped portion or a truncated wedge-shaped portion when viewed in a posterior-anterior direction.

9. The patellar implant of claim 1, wherein the at least one axis symmetric articulating surface defines an approximately wedge-shaped portion or a truncated wedge-shaped portion when viewed in a posterior-anterior direction.

10. The patellar implant of claim 1, further comprising a relived portion in a central region of the second surface.

11. The patellar implant of claim 1, wherein a shape of the at least one axis-symmetric articulating surface is substantially similar to or the same as a shape of a portion of a dome or button patellar component.

12. The patellar implant of claim 1, further comprising one or more reduced portions at the superior edge of the implant, the inferior edge of the implant, or both, configured to provide a smooth transition over a femoral component during flexion and extension.

13. The patellar implant of claim 1, wherein the at least one facet articulating surface scoops or extends concavely away from the at least one axis symmetric surface.

14. The patellar implant of claim 1, wherein the at least one axis symmetric articulating surface comprises two axis symmetric articulating surfaces, wherein a first of the two axis symmetric articulating surfaces generally extends from a central region in the medial direction and a second of the two axis symmetric articulating surfaces generally extends from the central region in the lateral direction.

15. A patellar implant comprising:
a patellar component body comprising a first surface configured to bear against a patella and a second surface configured to bear against a femoral component, wherein the second surface comprises:
at least two axis symmetric articulating surfaces that are positioned with respect to a central axis of the patellar component body that generally extends in an anterior-posterior direction, wherein each of the at least two axis symmetric articulating surfaces extends in a plane generally perpendicular to the central axis, and wherein a first of the at least two axis symmetric articulating surfaces generally extends from a central region toward a medial edge of the implant and a second of the at least two axis symmetric articulating surfaces generally extends from the central region toward a lateral edge of the implant;
at least two facet articulating surfaces located superior of the at least two axis symmetric articulating surfaces, wherein each of the at least two facet articulating surfaces generally extends in a superior-inferior direction and a medial-lateral direction;
wherein each of the at least two axis symmetric articulating surfaces is defined by a plurality of line segments within each surface, wherein the line segments are oriented to extend outwardly from the central axis and define curved line segments that are substantially the same such that each of the at least two axis symmetric articulating surfaces is rotationally symmetric about the central axis; and
wherein each of the at least two facet articulating surfaces is defined by a plurality of line segments within each surface, wherein the line segments are oriented to extend outwardly from the central axis and define line segments that are not substantially the same such that each of the at least two facet articulating surfaces is not rotationally symmetric about the central axis.

16. The patellar implant of claim 15, wherein the central region comprises a relieved portion that separates the first of the at least two axis symmetric articulating surfaces from the second of the at least two axis symmetric articulating surfaces.

17. The patellar implant of claim 15, wherein the at least two facet articulating surface are axis symmetric about a second axis.

18. The patellar implant of claim 17, wherein the second axis extends generally in the medial-lateral direction and is positioned posterior of the patellar implant.

19. The patellar implant of claim 15, wherein the plurality of line segments of each of the at least two axis symmetric articulating surfaces are substantially the same when viewed in a plurality of planes, each plane containing the central axis and one of the line segments of that axis symmetric articulating surface.

20. The patellar implant of claim 15, wherein the at least two facet articulating surfaces comprises four facet articulating surfaces.

21. The patellar implant of claim 20, wherein two of the four facet articulating surfaces are positioned superior of the at least two axis symmetric articulating surfaces and the other two of the four facet articulating surfaces are positioned inferior of the at least two axis symmetric articulating surfaces.

22. The patellar implant of claim 15, wherein each of the at least two axis symmetric articulating surfaces defines an approximately wedge-shaped portion or a truncated wedge-shaped portion when viewed in a posterior-anterior direction.

23. The patellar implant of claim 15, wherein a shape of each of the at least two axis-symmetric articulating surfaces is substantially similar to or the same as a shape of a portion of a dome or button patellar component.

* * * * *